United States Patent
Taghaddos

(10) Patent No.: US 6,939,354 B1
(45) Date of Patent: Sep. 6, 2005

(54) HAIR REMOVAL SYSTEM FOR USE PRIOR TO SKIN TREATMENT

(76) Inventor: Hamid Taghaddos, 428 Dudley Rd., Newton, MA (US) 02459

( * ) Notice: Subject to any disclaimer, the term of this patent is extended or adjusted under 35 U.S.C. 154(b) by 179 days.

(21) Appl. No.: 10/223,932

(22) Filed: Aug. 20, 2002

(51) Int. Cl.[7] .............................................. A61B 17/50
(52) U.S. Cl. ..................... 606/133; 606/131; 606/132; 606/134; 606/9
(58) Field of Search ................................ 606/131, 132, 606/133, 134, 9, 10, 13

(56) References Cited

U.S. PATENT DOCUMENTS

| | | | | |
|---|---|---|---|---|
| 5,190,558 A | * | 3/1993 | Ito | 606/131 |
| 5,470,332 A | * | 11/1995 | Mehl et al. | 606/36 |
| 5,827,294 A | * | 10/1998 | Mehl, Sr. | 606/133 |
| 5,921,890 A | * | 7/1999 | Miley | 606/2 |
| 6,104,959 A | * | 8/2000 | Spertell | 607/101 |
| 6,267,771 B1 | * | 7/2001 | Tankovich et al. | 606/131 |
| 6,471,712 B2 | * | 10/2002 | Burres | 606/131 |
| 6,666,836 B1 | * | 12/2003 | Islava | 602/2 |
| 6,689,143 B2 | * | 2/2004 | Cense et al. | 606/133 |

* cited by examiner

Primary Examiner—Glenn K. Dawson
Assistant Examiner—Michael Mendoza
(74) Attorney, Agent, or Firm—William Nitkin

(57) ABSTRACT

An accessory device attachable to a hand piece producing a beam for removal of hair from the skin of a patient prior to skin treatment on a body part, such device including a strip of material disposed between the hand piece and the patient's skin to interfer with the beam emitted from the hand piece to heat the surface of the skin under the material for burning only the hair and not the skin of the patient, such burnt hair adhering to the material. A method of removing hair from the skin of a body part of a patient prior to skin treatment on such body part is also disclosed.

4 Claims, 2 Drawing Sheets

HAIR REMOVAL SYSTEM FOR USE PRIOR TO SKIN TREATMENT

BACKGROUND OF THE INVENTION

1. Field of the Invention

The system and method of use of this invention reside in the area of hair removal prior to skin treatment and more particularly relate in one embodiment to an accessory device attachable to a hand piece producing a beam that generates heat, such accessory device providing a strip of material extending from a dispensing roll, under the beam between the hand piece and the patient's skin, to a take-up reel, such material causing the beam to burn only hair, such burnt hair adhering to the material which can then be rolled up on the take-up reel.

2. History of the Prior Art

Laser skin surgery for a variety of skin-related problems including, but not limited to, the removal of unwanted moles, warts, superficial basal cell carcinomas, wrinkles, tattoo removal and other cosmetic and medical laser surgery treatments must often be preceded by the removal of hair on or around the site of the laser treatment. This hair removal process prior to laser treatment can be accomplished by shaving or by the use of depilatory creams, both of which processes are messy and time-consuming. Hair removal can also be accomplished using flash lamp treatments wherein an electrical flash lamp is discharged close to the skin which procedure burns the hair off by the heat emitted from the electrical flash lamp. The burnt hair debris can then be removed by a vacuum cleaner system, such as disclosed in U.S. Pat. No. 6,187,001 to Azar et al. Such system, though, requires an additional complex and costly electronic apparatus.

SUMMARY OF THE INVENTION

It is an object of this invention in one embodiment to provide an inexpensive and simple accessory device for use in conjunction with a hand piece producing a beam that generates heat for the non-permanent removal of hair at the site of skin treatment prior to such treatment. In some embodiments where the hair root is heated sufficiently, the hair root dies and the hair removal process is permanent. The device in a further embodiment can be an accessory device that releasably attaches to a hand piece, such as a laser hand piece, and utilizes a strip of material web provided on a dispensing roll which material passes under the laser beam and contacts the skin of the patient. The beam strikes the material at a heat level that is sufficiently strong to heat and burn the hair on the surface of the skin without burning the skin, which burnt hair adheres to the strip of material. The strip of material with burnt hair adhered thereto can then be, in one embodiment, rolled up on a take-up reel and removed from the treatment site. After use, or when desired, the dispensing roll and the take-up reel can be removed from their respective shaft supports and replaced with a new dispensing roll or material and new take-up reel. The accessory device can, in one embodiment, be then removed from the hand piece so that the laser treatment or other treatment can then proceed without any interference from the presence of hair at the treatment site. In other embodiments the accessory device can be moved out of the way of the treatment beam after the hair has been removed.

DESCRIPTION OF THE PREFERRED EMBODIMENT(S)

Figure 1:
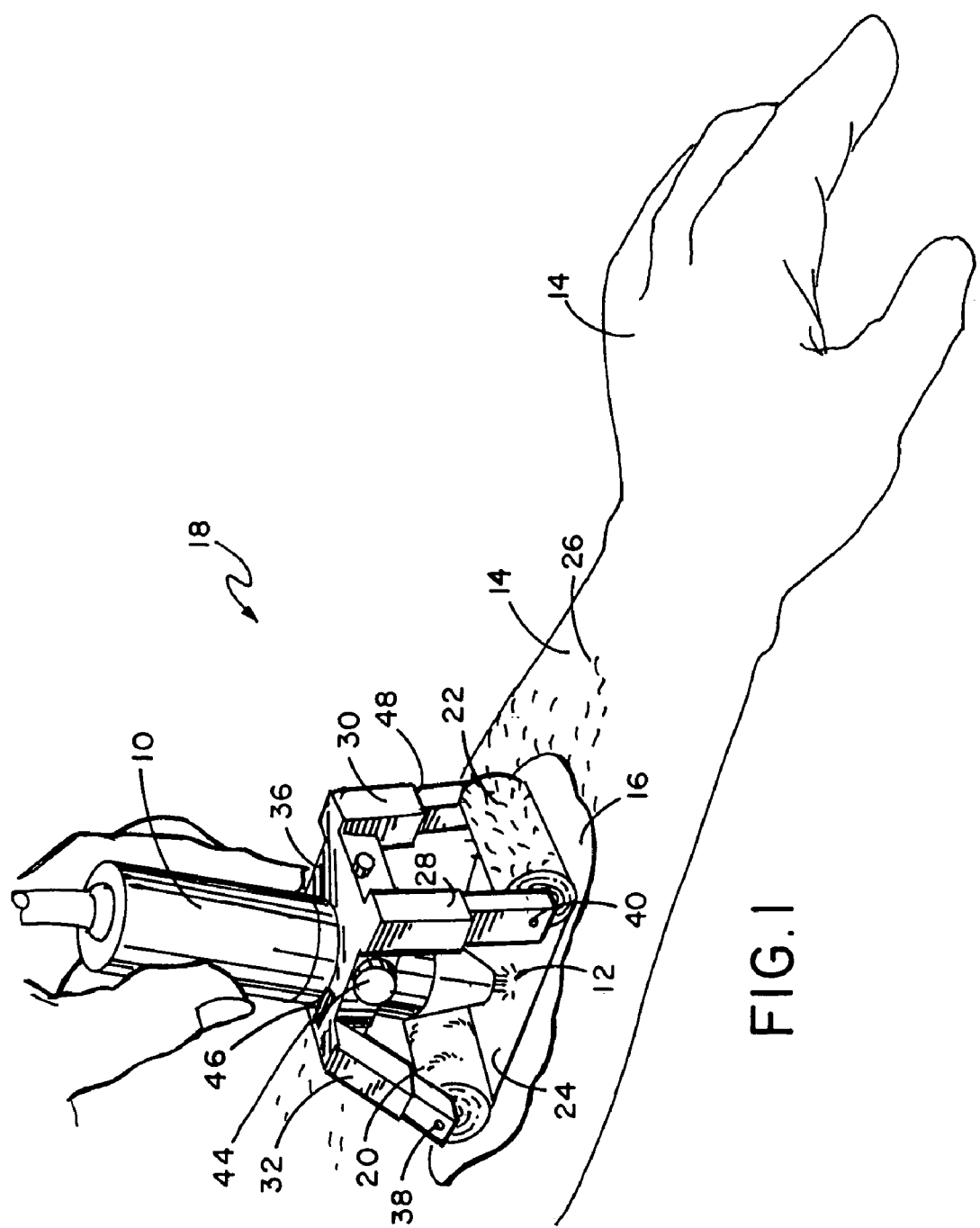
FIG. 1 illustrates a perspective view of the accessory device of this invention mounted on a laser hand piece with the material strip positioned on the skin of a patient.
Figure 2:
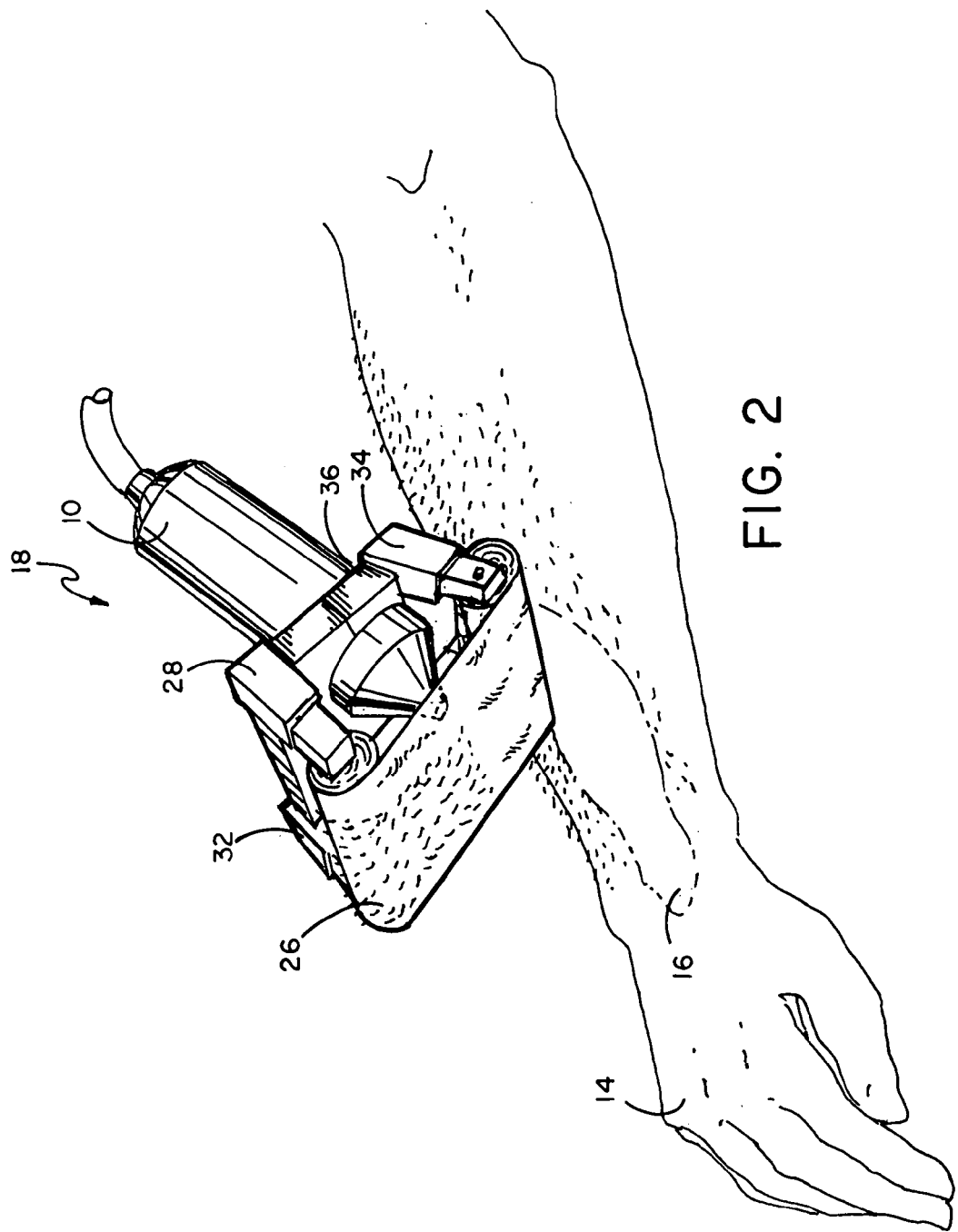
FIG. 2 illustrates a close-up perspective view of a section of the laser hand piece of FIG. 1 in a tilted position showing the burnt hair adhered to the material strip as it is rolled up onto the take-up reel.

FIG. 1 illustrates a perspective view of a laser hand piece 10 disposed over a body part 14 of a patient about to undergo, for example, laser skin treatment. Other types of heat beams can be used, and the discussion of the use of laser treatment herein is only exemplary. Laser hand piece 10 produces a laser beam 12 directed against a strip or length of material 24 which can be a web-like material, a fabric, a cellulose-based product, a perforated sheet of plastic or any other material suitable for accomplishing the laser beam interference but sufficient to allow the heat of the laser beam to burn off hair under the material with the residue of the burnt hair retained on the material and then removed by the advancement of the material under the beam. Material 24 can be provided from a dispensing roll 20 to a take-up reel 22, and material 24 should be at least as wide as the width of beam 12. Some laser beams are approximately 1 square centimeter in area. The dispensing and take-up process can be accomplished manually, for example, by using a wind-up handle or can be accomplished using electric motor power. Dispensing roll 20 can be supported on first shaft support 32 and second shaft support 34 which engage and rotatably retain the central shaft 38 of dispensing roll 20. The upper portions of first and second shaft supports 32 and 34 are retained on one side of removable structure 36 which surrounds laser hand piece 10. In the same manner third and fourth shaft supports 28 and 30 rotatably retain central shaft 40 of take-up reel 22. Equivalent means of attaching the accessory device of this invention to the laser hand piece can also be provided.

During such hair removal procedures a cooling gel or cream 16 is applied to body part 14 of the patient before laser beam 12 is directed at material 24, sufficiently heating material 24 and body part 14 to cause the burning off of hair 26 from body part 14 such that the burnt hair becomes adhered to material 24 which can be then rolled up on take-up reel 22, thus removing the hair from the site of the laser treatment. Laser beam 12 does not burn the underlying skin. After the hair has been removed using the accessory device of this invention, the accessory device can be either moved out of the way or removed from the laser hand piece to allow the laser treatment of the skin to be carried out.

It should be noted that other heat beam-producing devices can be used with the structure of this invention, for example, laser hand piece 10 can be replaced by a hand piece producing radio waves, light waves and the like as long as such beams produce sufficient heat for hair removal. Seen in FIG. 1 is adjustment knob 44 which allows for the positioning of laser hand piece 10 at a higher or lower position within accessory device 18. Further, first, second, third and fourth shaft supports 32, 34, 28 and 30 can be adjusted in height at telescopic junctions, such as junction 48. Dispensing roll 20 and take-up reel 22 can be motor-driven by having a motor and gear works, not shown, disposed within accessory device 18 which motor can be turned on or off by switch 46. Other embodiments of accessory device 18 can use a gear-driven friction movement against body part 14 to advance material 24 from dispensing roll 20 to take-up reel 22. It should be further noted that the device of this invention can be used not only for hair removal, but also for other procedures such as tattoo removal and the like.

Although the present invention has been described with reference to particular embodiments, it will be apparent to those skilled in the art that variations and modifications can be substituted therefor without departing from the principles and spirit of the invention.

I claim:

1. A device in combination with a hand piece producing a beam for the removal of hair from the skin of a body of a patient prior to skin treatment, comprising:
    a material adapted to be disposed between said hand piece and said body of the patient, such material interfering with said beam sufficiently to cause heating and burning of said hair but not burning of said skin, said burnt hair adhering to said material for the removal thereof, wherein said device is removably attached to said hand piece, and said device further including a dispensing roll for dispensing said material.

2. A hair removal system for the removal of hair from the skin of a body part of a patient prior to skin treatment on said body part, comprising:
    a hand piece, said hand piece emitting a beam; and
    a material adapted to be disposed between said hand piece and the body part of said patient, said material interfering with said beam directed at said body part through said material, said beam creating heat under said material to burn the hair on said body part but not burn the skin, said burnt hair adhering to said material, said device further including means to move said material under said beam, said material picking up said burnt hair as it is moved wherein said means to move said material comprises a dispensing roll for dispensing said material and a take-up reel for taking up said material, said dispensing roll and take-up reel attachable on opposite sides of said hand piece, said material to be moved from said dispensing roll, between said hand piece and said body part of the patient under said beam, to said take-up reel.

3. A method of removing hair from the skin of a body part of a patient prior to skin treatment on said body part, comprising the steps of:
    providing a piece of material;
    placing said material on the skin of said body part;
    providing a hand piece producing a beam;
    directing said beam through said material;
    interfering with said beam by said material;
    heating and burning said hair on said body part under said material by said beam without burning said skin sufficiently to cause said burnt hair to adhere to said material;
    removing said material with burnt hair adhered thereto;
    providing a length of said material;
    providing said length of material in a roll form;
    providing a dispensing roll for dispensing said length of material therefrom;
    providing a take-up reel for taking up said length of material; and
    rolling up said length of material with said burnt hair adhered thereon on said take-up reel.

4. The method of claim 3 further including, before the step of placing said material on the skin of said body part, the step of applying a cooling gel to the skin of said body part.

* * * * *